United States Patent
Beebe et al.

(10) Patent No.: US 8,389,294 B2
(45) Date of Patent: Mar. 5, 2013

(54) MICROFLUIDIC DEVICE AND METHOD FOR COUPLING DISCRETE MICROCHANNELS AND FOR CO-CULTURE

(75) Inventors: David J. Beebe, Monona, WI (US); Jay W. Warrick, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 1304 days.

(21) Appl. No.: 12/135,629

(22) Filed: Jun. 9, 2008

(65) Prior Publication Data

US 2009/0305326 A1    Dec. 10, 2009

(51) Int. Cl.
*G01N 15/06* (2006.01)
*G01N 33/00* (2006.01)
*G01N 33/48* (2006.01)

(52) U.S. Cl. ......... 436/180; 422/50; 422/68.1; 422/81; 422/82; 422/502; 422/503; 422/504; 422/507; 436/43

(58) Field of Classification Search .......... 422/68.1, 422/50, 81, 82, 502, 503, 504, 507; 436/43, 436/180
See application file for complete search history.

(56) References Cited

U.S. PATENT DOCUMENTS

| | | | |
|---|---|---|---|
| 6,012,902 A | 1/2000 | Parce | |
| 6,090,251 A | 7/2000 | Sundberg et al. | |
| 6,171,067 B1 | 1/2001 | Parce | |
| 6,174,675 B1 | 1/2001 | Chow et al. | |
| 6,210,128 B1 | 4/2001 | Rife et al. | |
| 6,224,728 B1 | 5/2001 | Oborny et al. | |
| 6,262,519 B1 | 7/2001 | Furlani et al. | |
| 6,274,089 B1 | 8/2001 | Chow et al. | |
| 6,296,452 B1 | 10/2001 | Caren | |
| 6,318,970 B1 | 11/2001 | Backhouse | |
| 6,368,562 B1 | 4/2002 | Yao | |
| 6,739,576 B2 | 5/2004 | O'Connor et al. | |
| 6,767,706 B2 | 7/2004 | Quake et al. | |
| 6,949,176 B2 | 9/2005 | Vacca et al. | |
| 7,156,969 B2 | 1/2007 | Mehta et al. | |
| 2003/0203506 A1 | 10/2003 | Beebe et al. | |
| 2004/0115830 A1 | 6/2004 | Touzov | |

OTHER PUBLICATIONS

"Macro-to-Micro Interfaces for Microfluidic Devices", Miniaturization for Chemisty, Biology & Bioengineering; vol. 4, pp. 526-533, Jul. 13, 2004, by Carl K. Fredrickson and Z. Hugh Fan.
"Well-Plate Formats and Microfluidics-Applications of Laminar Fluid Diffusion Interfaces to HTP Screening", Micro Total Analysis Systems 2001, pp. 383-384, by Bernard H. Weigl et al.

*Primary Examiner* — Brian J Sines
(74) *Attorney, Agent, or Firm* — Boyle Fredrickson, S.C.

(57) ABSTRACT

A microfluidic device and method is provided for coupling discrete channels and for co-culture. The microfluidic device includes first and second bodies. Each body has a bottom surface and defines a channel. The channel in each body includes an inlet and an outlet communicating with the bottom surface. A first fluid, such as a first cell suspension, is provided within the channel of the first body and a second fluid, such a second cell suspension, is provided within the channel of the second body. The first and second bodies are movable between a first position wherein the outlet of the channel of the first body is spaced from the inlet of the channel of the second body and a second position wherein the fluid at the outlet of the channel of the first body communicates with the fluid at the inlet of the channel of the second body.

7 Claims, 5 Drawing Sheets

MICROFLUIDIC DEVICE AND METHOD FOR COUPLING DISCRETE MICROCHANNELS AND FOR CO-CULTURE

REFERENCE TO GOVERNMENT GRANT

This invention was made with United States government support awarded by the following agencies: NIH CA104162. The United States government has certain rights in this invention.

FIELD OF THE INVENTION

This invention relates generally to microfluidic devices, and in particular, to a microfluidic device and method for co-culturing cells and for simply and easily coupling discrete microchannels of the device.

BACKGROUND AND SUMMARY OF THE INVENTION

Microfluidics offers the precise control of many parameters of cellular micro-environments including fluid shear stress, diffusion of soluble factors, and patterning of cells and extracellular matrix. Microfluidic devices have been used to explore a variety of biological problems of interest, ranging from fundamental research in protein crystallization to diagnostic assays. As such, microfluidic devices are becoming a part of many new approaches to investigating cell behavior and interaction. On the micro-scale, certain physical phenomena and interactions play a much more significant role in system behavior when compared to the macro-scale. Developing new microchannel designs and methods will allow for more robust control of the micro-environment and system parameters leading to improved analysis.

As is known, cells do not live in isolation. In all multi-cellular organisms, such as the human body, the cells within the body continually receive and send signals that coordinate the growth, differentiation, and metabolism of the cells in diverse tissues and organs. For example, morphogens are signaling molecules secreted by cells. In embryos, concentration gradients of morphogens play a key role in the formation and differentiation of many tissues, as well as, set the stage for the formation of organs. Further, it has been found that more intricate structures are formed by local, and sometimes reciprocal, interactions between different cell types. For example, the hair follicle is formed and maintained according to reciprocal signaling between the epidermal and dermal components of the skin. Reciprocal interactions also take place in the nervous system during formation of axon scaffolds that are precursors to neuronal connections, as well as, in regeneration wherein glial signals can, in fact, be detrimental to the repair process. As such, it can be appreciated that a better understanding of tissue level signaling is important for the development of new therapies and for tissue engineering. In addition, robust tools for in vitro modeling may have utility for the discovery of new drugs that target signaling pathways.

To study reciprocal signaling in vitro, one can employ cells that either over-express a component of a pathway or have dominant negative allele. However, this process requires the prior knowledge (or at least a hint) of the pathways involved. Also, genetic manipulations are difficult if the interaction between the cells involves multiple pathways. Pharmacological inhibitors could be used, but these inhibitors are only available for some signaling cascades and tend to lack specificity.

An alternative way of studying reciprocal signaling is to observe two or more cell types involved as they are joined in co-culture or separated after having been in contact. Traditional co-culture techniques do not enable easy cessation of cell to cell communication within a co-culture. In a mixed co-culture, it is not possible to remove all signals originating with one cell type, while leaving the second cell type unaffected. For example, when using filter well inserts, cells are usually seeded on either side of a membrane. It can be appreciated that any effort to remove one cell type from a well is likely to disturb the other cell type. Even if one cell type is seeded on the bottom of a well and the other on a filter insert, it will be difficult and time consuming to remove the filter without causing crosstalk between the wells.

Further, it has been found that disparate cell types can be difficult to co-culture due to each cell types individual needs for stringent culture conditions. In addition, different cell types often develop and mature at different rates. As a result, roadblocks to the development of appropriate physiologically relevant connections between the cell types may be created if the cell types are initially cultured at the same point in time.

Therefore, it is a primary object and feature of the present invention to provide a microfluidic device and method for co-culturing cells in discrete channels of a microfluidic device.

It is a further object and feature of the present invention to provide a microfluidic device and a method for selectively coupling discrete channels of the device.

It is a still further object and feature of the present invention to provide a microfluidic device and a method that allows for cells to be simply and easily removed from a channel of a microfluidic device.

In accordance with the present invention, a microfluidic device is provided. The microfluidic device includes a first body having bottom surface and defining a channel. The channel includes an inlet and an outlet communicating with the bottom surface. A first fluid is provided within the channel of the first body. The first fluid has a radius of curvature at the outlet. The microfluidic device also includes a second body having an upper surface and defining a channel. The channel of the second body includes an inlet communicating with the upper surface and an outlet. A second fluid is provided within the channel of the second body. The second fluid has a radius of curvature at the inlet. The first and second bodies are movable between a first position wherein the outlet of the channel of the first body is spaced from the inlet of the channel of the second body and a second position wherein the fluid at the outlet of the channel of the first body communicates with the fluid at the inlet of the channel of the second body.

The first fluid has a surface tension at the outlet of the first body with the first and second bodies in the first position. The surface tension of the first fluid maintains the first fluid within the channel of the first body with the first and second bodies in the first position. The first body includes an upper surface and the inlet of the channel of the first body communicates with the upper surface of the first body. The fluid at the inlet of the channel in the first body has a radius of curvature less than the radius of curvature of the fluid at the outlet of the channel in the first body.

In accordance with a further aspect of the present invention, a method of co-culturing cells is provided. The method includes the step of providing a channel network in a first microfluidic device. The channel network includes a channel having an input and an output. The first channel is filled with a first media. A channel network is provided in a second microfluidic device. The channel network in the second microfluidic device includes a channel having an input and an output. The channel in second microfluidic device is filed with a second media. The first media at the output of the channel of the first microfluidic device is brought into contact with the second media at the input of the channel of the second microfluidic device.

The method may include the additional step of depositing a drop on the input of the channel of the first microfluidic device so as to generate the flow of the first media from the input of the channel of the first microfluidic device to the output of the channel of the first microfluidic device. The drop at the input of the channel of the first microfluidic device has a radius of curvature less than the radius of curvature of the first media at the output of the channel of the first microfluidic device. In addition, it is contemplated for the drop at the input of the channel of the first microfluidic device to have a radius of curvature less than the radius of curvature of the second media at the output of the channel of the second microfluidic device. The method may also include the step of disengaging the first media at the output of the channel of the first microfluidic device from the second media at the input of the channel of the second microfluidic device.

The first media includes a first set of cells and the second media includes a second set of cells. The interaction of the first and second sets of cells are observed after the step of bringing the first media in contact with the second media.

In accordance with a still further aspect of the present invention, a method of coupling a channel in a first body and a channel in a second body is provided. Each channel includes an input and an output. The method includes the steps of providing a drop at the output of the channel of the first body and providing a drop at the input of the channel of the second body. The drop at the output of the channel of the first body is brought into contact with the drop at the input of the channel of the second body.

The method may include the additional steps of filling the channel of the first body with a first media and filling the channel of the second body with a second media. A drop is deposited on the input of the channel of the first body so as to generate the flow of the first media from the input of the channel of the first body to the output of the channel of the first body. The drop on the input of the channel of the first body has a radius of curvature less than the radius of curvature of the first media at the output of the channel of the first body. In addition, the drop on the input of the channel of the first body may have a radius of curvature less than the radius of curvature of the second media at the output of the channel of the second body.

The drop at the output of the channel of the first body may be disengaged from the drop at the input of the channel of the second body. It is contemplated for the drop at the output of the channel of the first body to include a first set of cells and for the drop at the input of the channel of the second body to include a second set of cells. The interaction of the first and second sets of cells after the step of bringing the drop at the output of the channel of the first body into contact with the drop at the input of the channel of the second body is observed.

BRIEF DESCRIPTION OF THE DRAWINGS

The drawings furnished herewith illustrate a preferred construction of the present invention in which the above advantages and features are clearly disclosed as well as others which will be readily understood from the following description of the illustrated embodiment.

In the drawings.

DETAILED DESCRIPTION OF THE DRAWINGS

Figure 1:
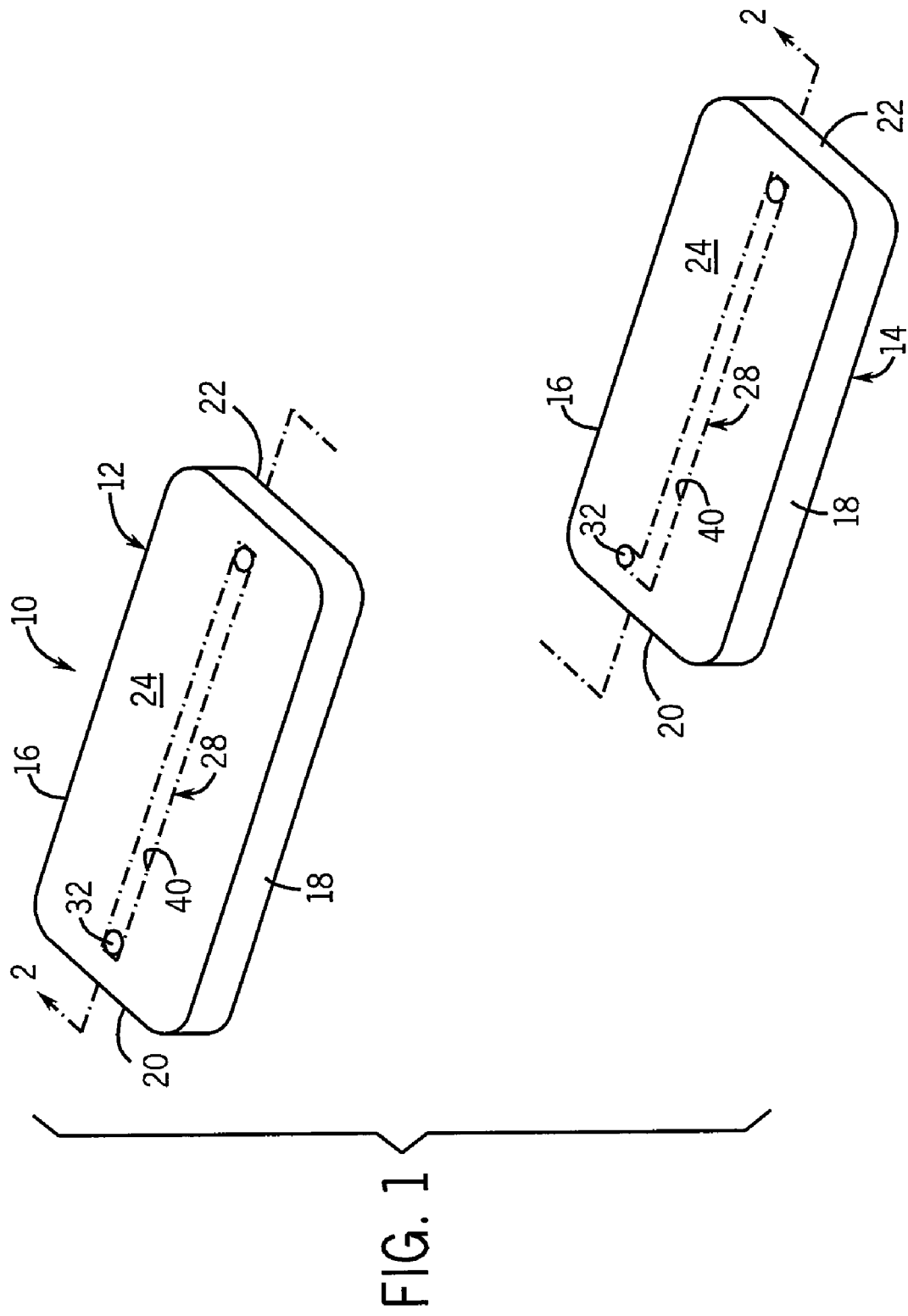
FIG. 1 is an isometric view of a microfluidic device in accordance with the present invention.
Figure 2:
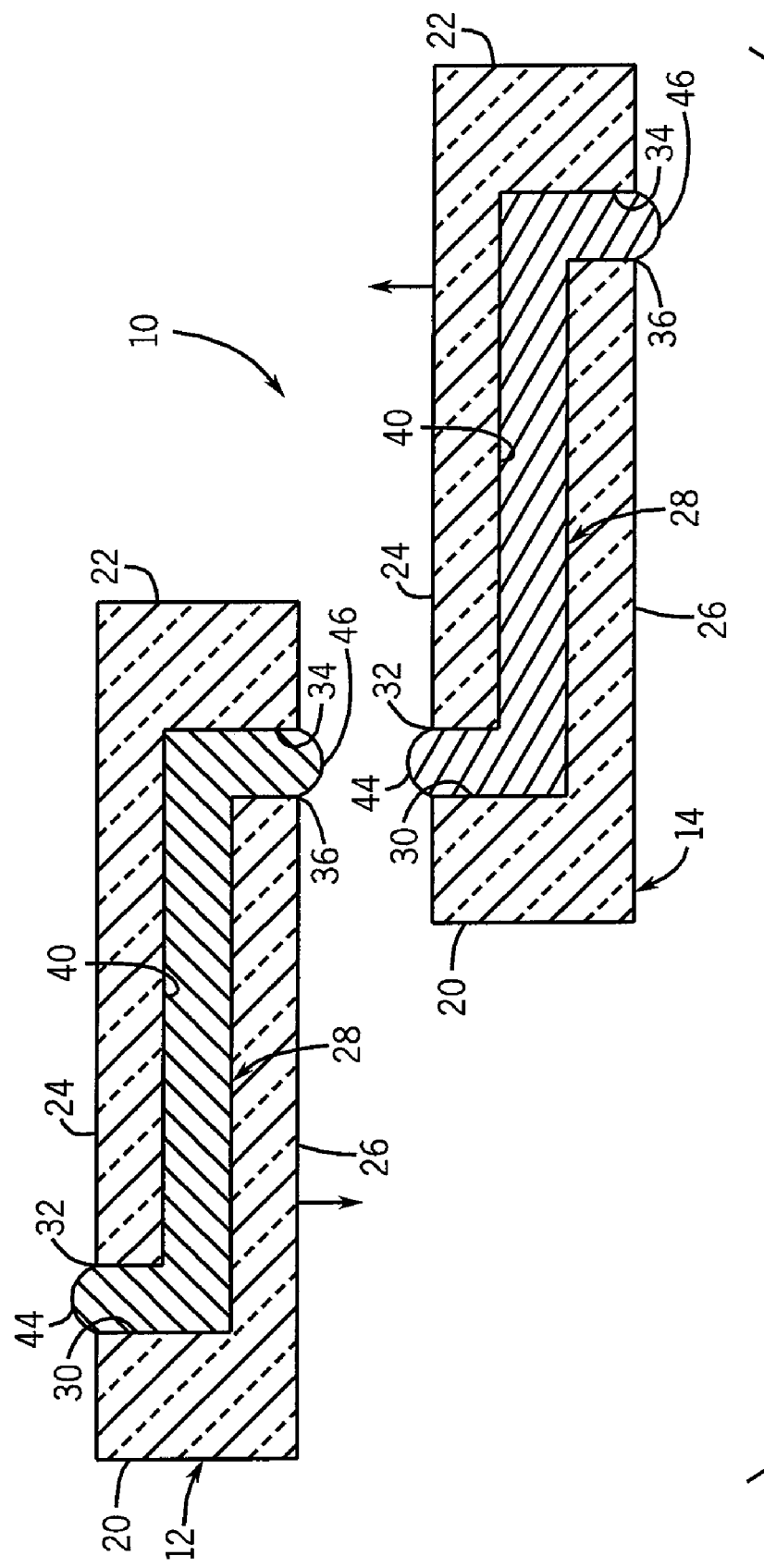
FIG. 2 is a cross sectional view of the device of the present invention taken along line 2-2 of FIG. 1 showing the first and second bodies of the device in a disengaged position.

Referring to FIGS. 1-2, a microfluidic device for use in the method of the present invention is generally designated by the reference numeral 10. Microfluidic device 10 includes first and second bodies 12 and 14, respectively, formed from any suitable material such as polydimethylsiloxane (PDMS). First and second bodies 12 and 14, respectively, are identical in structure. As such, the following description of first body 12 is understood to describe second body 14 as if fully described hereinafter.

First body 12 has first and second sides 16 and 18, respectively, and first and second ends 20 and 22, respectively. First body 12 further includes upper and lower surfaces 24 and 26, respectively. Channel 28 extends through first body 12 of microfluidic device 10 and includes a first vertical portion 30 terminating at an input port 32 that communicates with upper surface 24 of first body 12 and a second vertical portion 34 terminating at an output port 36 communicating with lower surface 26 of first body. First and second vertical portions 30 and 34, respectively, of channel 28 are interconnected by and communicate with horizontal portion 40 of channel 28. The dimension of channel 28 connecting input port 32 and output port 36 is arbitrary. In the depicted embodiment, the input ports and output ports of microfluidic device 10 have generally circular configurations. However, alternate configurations, such as slit-shaped and oval ports, are possible without deviating from the scope of the present invention.

It is intended to fill channels 28 of first and second bodies 12 and 14, respectively, with a predetermined gel, fluid or liquid, as hereinafter described. As is known, the amount of pressure present within a drop of liquid at an air-liquid interface is given by the Young-LaPlace equation:

$$\Delta P = \gamma(1/R1 + 1/R2) \quad \quad \text{Equation (1)}$$

wherein $\gamma$ is the surface free energy of the liquid; and R1 and R2 are the radii of curvature for two axes normal to each other that describe the curvature of the surface of a drop.

For spherical drops, Equation (1) may be rewritten as:

$$\Delta P = 2\gamma/R \quad \quad \text{Equation (2)}$$

wherein: R is the radius of a spherical first drop.

From Equation (2), it can be seen that smaller drops have a higher internal pressure than larger drops. Therefore, if two drops having different radii of curvature are connected via a fluid-filled tube (i.e. channel 28), the drop with the smaller radius of curvature will shrink while the larger one grows in size. One manifestation of this effect is the pulmonary phenomenon called "instability of the alveoli" which is a condition in which large alveoli continue to grow while smaller ones shrink. As described, fluid can be pumped through channel 28 by using the surface tension in first and second drops 44 and 46, respectively, on corresponding input and output ports 32 and 36, respectively, of channel 28.

Further, it is contemplated to etch patterns in upper surface 24 of first body 12 about the outer periphery of input port 32 and/or to etch patterns in lower surface 26 of first body 12 about the outer periphery of output port 36 in order to alter the corresponding configurations of first and second drops 44 and 46, respectively, deposited thereon. By altering the configurations of first and second drops 44 and 46, respectively, it can be appreciated that the volumetric flow rate of fluid through channel 28 of first body 12 may be modified. In addition, by etching the patterns in upper surface 24 of first body 12, it can be appreciated that the time period during which the pumping of the fluid through channel 28 of first body 12 takes place may be increased or decreased to a user desired time period.

In operation, channel 28 of first body 12 may be filled with a fluid such as a cell suspension such that second drop 46 is provided at output port 36 of channel 28, FIG. 2. Second drop 46 may be deposited at output port 36 of channel 28, if so desired. First drop 44 having a radius of curvature smaller than the radius of curvature of second drop 46 is deposited on input port 32 of channel 28. First drop 44 may be hemispherical in shape or may be other shapes. As such, it is contemplated that the shape and the volume of first drop 44 be defined by the hydrophobic/hydrophilic patterning of the surface surrounding input port 32. As heretofore described, first body 12 is formed from PDMS which has a high hydrophobicity and has a tendency to maintain the shapes of first and second drops 44 and 46, respectively, on input and output ports 32 and 36, respectively. The surface tension of second drop 46 at output port 36 of first body 12 maintains the fluid within channel 28. It is contemplated as being within the scope of the present invention that the fluid in channel 28, first drop 44 and second drop 46 be the same or different fluids.

Because first drop 44 has a smaller radius of curvature than second drop 46, a larger pressure exists on the input port 32 of channel 28. The resulting pressure gradient causes first drop 44 to flow from input port 32 through channel 28 towards second drop 46 over output port 36 of channel 28. It can be understood that by sequentially depositing additional drops 44 on input port 32 of channel 28, the resulting pressure gradient will cause the drops 44 deposited on input port 32 to flow through channel 28 towards second drop 46 at output port 36 of channel 28. As a result, the fluid flows through channel 28 from input port 32 to output port 36. Given that output port 36 is positioned below horizontal portion 40 of channel 28, it can be appreciated that the fluid flowing through channel 28 will allow a user to remove any cell or molecules suspended within the fluid within channel 28.

Alternatively, channel 28 of second body 14 may be filled with a fluid such as a cell suspension such that second drop 46 is provided at output port 36 of channel 28 of second body, FIG. 2. It is noted that channels 28 of first and second bodies 12 and 14, respectively, may be filled contemporaneously or at separate time periods. Further, the fluid used to fill channel 28 of second body 14 may be the same of different than the fluid used to fill first body 12. Second drop 46 may be deposited at output port 36 of channel 28, if so desired. First drop 44 having a radius of curvature smaller than the radius of curvature of second drop 46 is deposited on input port 32 of channel 28 of second body 14. First drop 44 on input port 32 of channel 28 of second body 14 may be hemispherical in shape or may be other shapes. As such, it is contemplated that the shape and the volume of first drop 44 on input port 32 of channel 28 of second body 14 to be defined by the hydrophobic/hydrophilic patterning of the surface surrounding input port 32. As heretofore described, second body 14 is formed from PDMS which has a high hydrophobicity and has a tendency to maintain the shapes of first and second drops 44 and 46, respectively, on input and output ports 32 and 36, respectively, of second body 14. The surface tension of second drop 46 at output port 36 of second body 14 maintains the fluid within channel 28. It is contemplated as being within the scope of the present invention that the fluid in channel 28, first drop 44 and second drop 46 be the same or different fluids.

Figure 3:
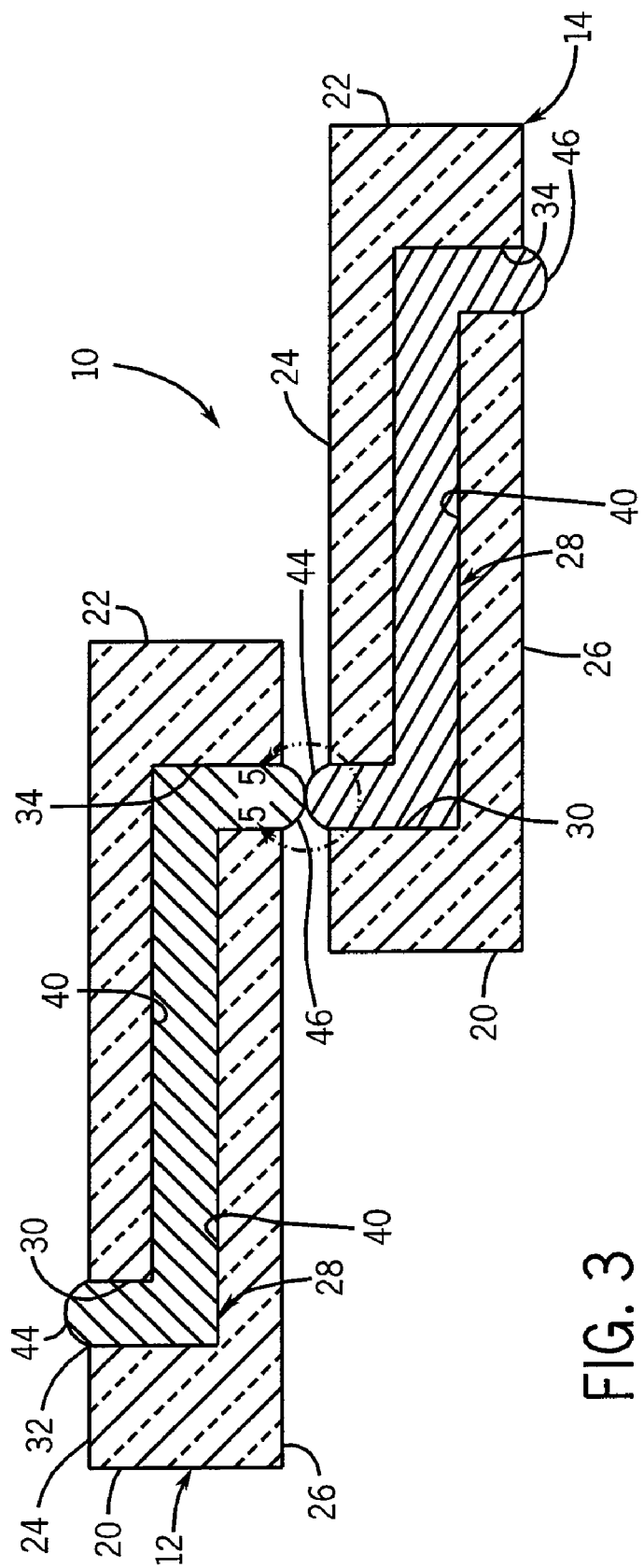
FIG. 3 is a cross sectional view of the device of the present invention, similar to FIG. 2, showing the first and second bodies of the device in an engaged position.
Figure 5:
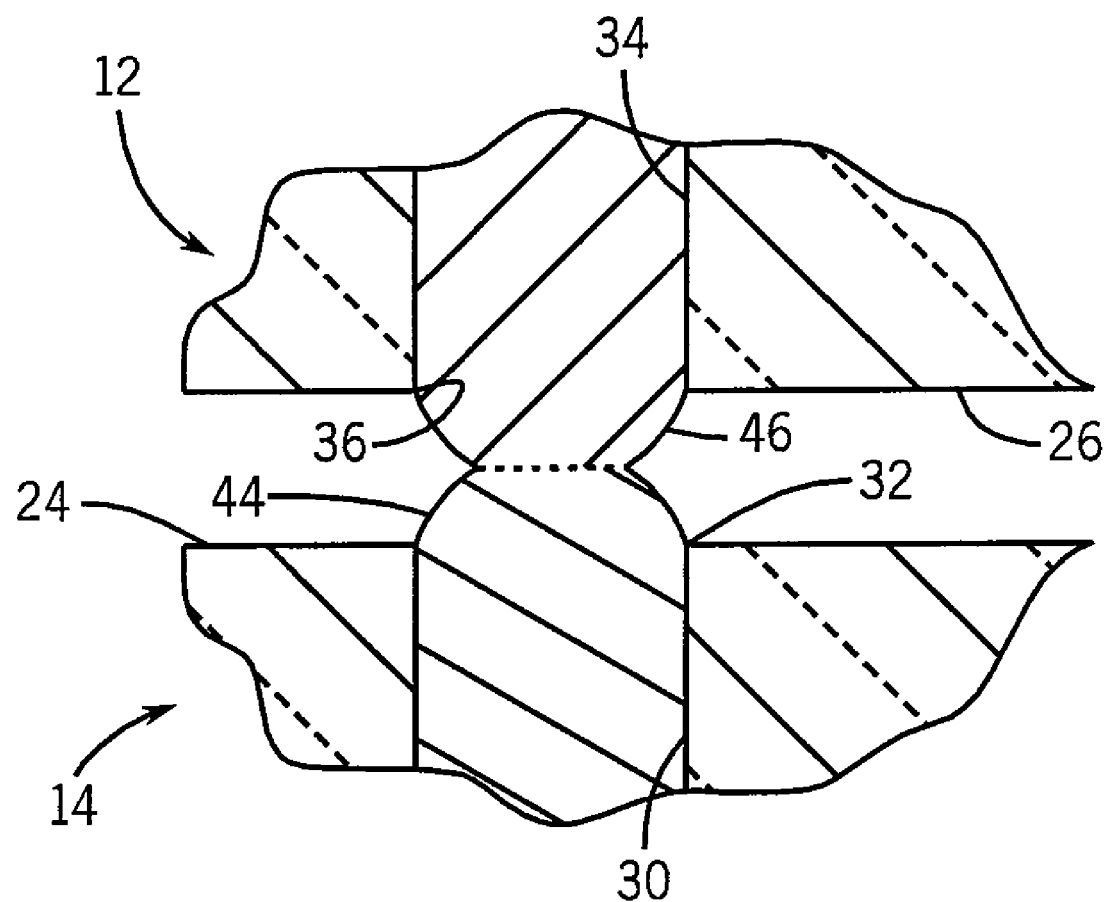
FIG. 5 is an enlarged, cross sectional view of the device of the present invention taken along line 5-5 of FIG. 3.

Once channel 28 of second body 14 is filled, the cells in the cells suspensions received in channels 28 of first and second bodies 12 and 14, respectively, are allowed to develop up to a desired point. The staggered introduction of the cells in channels 28 of first and second bodies 12 and 14, respectively, allows for improved interaction between cells that develop at different rates. Thereafter, output port 36 of first body 12 is aligned with input port 32 of second body 14 and first body 12, second body 14 and/or both are moved axially such that second drop 46 at output port 36 of first body 12 engages and is in fluid contact with first drop 44 at input port 32 of second body 14, FIG. 3. As best seen in FIG. 5, with second drop 46 at output port 36 of first body 12 in engagement with first drop 44 at input port 32 of second body 14, interface 50 is formed at the intersection thereof. The shape and configuration of interface 50 is relatively predictable and clearly defined. It can be appreciated that the predictable interface allows for the study of reactions at the boundary of the first and second drops 44 and 46, respectively. In addition, the stable interface and ability to neatly decouple first and second drops 44 and 46, respectively, allows the methodology of the present invention to be utilized in a variety of applications. For example, the methodology of the present invention may be used to couple a channel to a conventional array so as to provide a major savings in time and reagents in high-throughput co-culture. Further, as described, microfluidic device 10 of the present invention allows for disparate cell types to be co-cultured in different media in channels 28 of first and second bodies 12 and 14, respectively, while allowing physiological communication between the cells.

After a predetermined period of time, it is contemplated to axially move first body 12, second body 14 and/or both so as to separate second drop 46 at output port 36 of first body 12 from first drop 44 at input port 32 of second body 14, FIG. 2. Thereafter, a user may independently study the interaction of the cells cultured in channel 28 of first body 12 and those cultured in channel 28 of second body 14. Alternatively, the cell suspensions in channel 28 of first body 12 and/or the cell suspension in channel 28 of second body 14 may be brought into fluid contact with a still further cell suspension in a third body (not shown) in the manner heretofore described.

Figure 4:
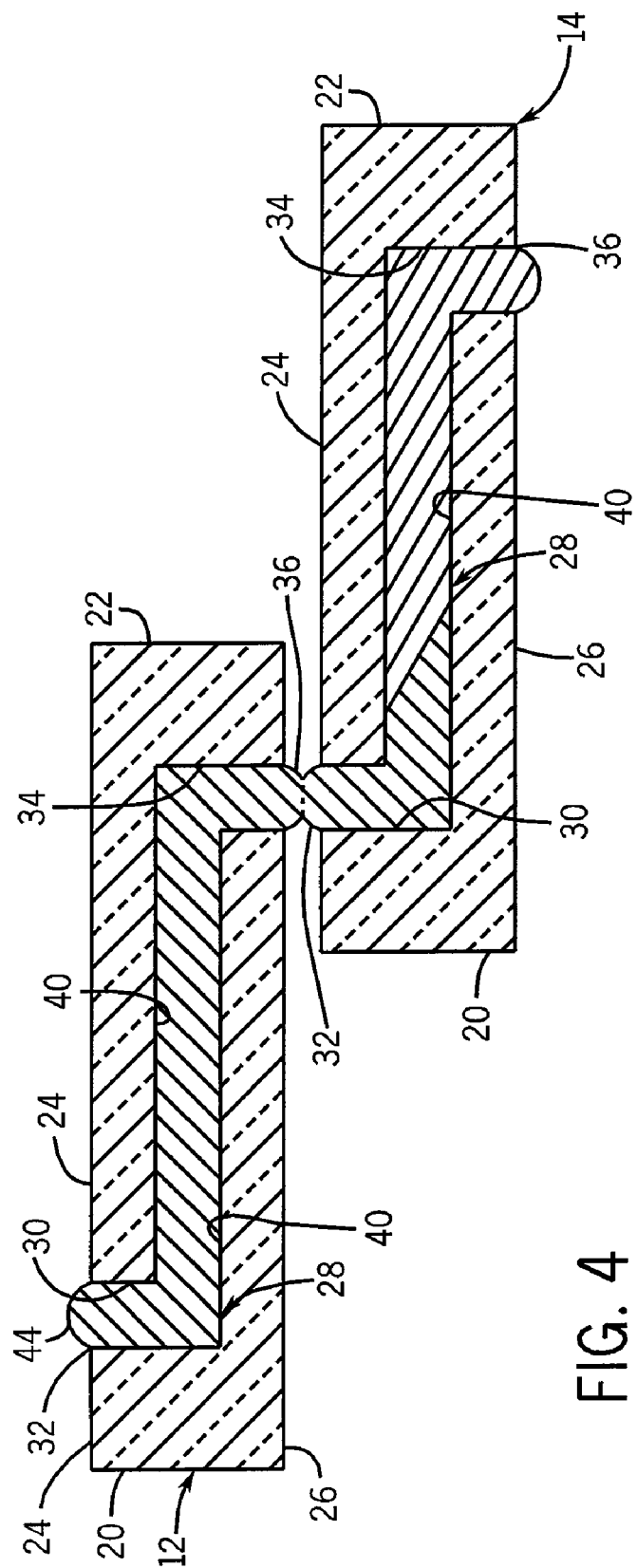
FIG. 4 is a cross sectional view of the device, similar to FIG. 3, showing the first and second bodies of the device in an engaged position with fluid flowing therethrough.

Referring to FIG. 4, it is contemplated to utilize microfluidic device 10 of the present invention to move the cell suspension provided in channel 28 of first body 12 into the channel of an alternate body, e.g., channel 28 of second body 14. More specifically, in the depicted embodiment, output port 36 of first body 12 is aligned with input port 32 of second body 14 and first body 12, second body 14 and/or both are moved axially such that second drop 46 at output port 36 of first body 12 engages and is in fluid contact with first drop 44 at input port 32 of second body 14. First drop 44 at input port 32 of first body 12 has a radius of curvature smaller than the radius of curvature of second drop 46 at the output port 36 of second body 14. Because first drop 44 at input port 32 of first body 12 has a smaller radius of curvature than second drop 46 at the output port 36 of second body 14, a larger pressure exists on the input port 32 of first body 12. The resulting pressure gradient causes first drop 44 to flow from input port 32 of first body 12; through channel 28 of first body 12; through output port 36 of first body 12; through input port 32 of second body 14; and through channel 28 in second body 14 towards second drop 46 at output port 36 of second body 14. It can be understood that by sequentially depositing additional drops 44 on input port 32 of first body 12 will cause the cell suspension in channel 28 of first body 12 to flow into channel 28 of second body 14.

Various modes of carrying out the invention are contemplated as being within the scope of the following claims particularly pointing out and distinctly claiming the subject matter which is regarded as the invention.

We claim:

1. A method of fluidically coupling a channel in a first body and a channel in a second body, each channel including an input and an output, the method comprising the steps of:
   providing a drop at the output of the channel of the first body;
   providing a drop at the input of the channel of the second body; and
   moving at least one of the first body and the second body from a first position wherein the outlet of the channel of the first body is spaced from the input of the channel of the second body and a second position wherein the drop at the output of the channel of the first body is in contact with the drop at the input of the channel of the second body such that the channel in the first body is fluidically coupled to the channel in the second body.

2. The method of claim 1 comprising the additional steps of:
   filling the channel of the first body with a first media; and
   filling the channel of the second body with a second media.

3. The method of claim 2 comprising the additional step of depositing a drop on the input of the channel of the first body so as to generate the flow of the first media from the input of the channel of the first body to the output of the channel of the second body.

4. The method of claim 3 wherein the drop on the input of the channel of the first body has a radius of curvature less than the radius of curvature of the first media at the output of the channel of the first body.

5. The method of claim 3 wherein the drop on the input of the channel of the first body device has a radius of curvature less than the radius of curvature of the second media at the output of the channel of the second body.

6. The method of claim 1 comprising the additional step of disengaging the drop at the output of the channel of the first body from the drop at the input of the channel of the second body.

7. The method of claim 2 wherein:
   the first media in the channel of the first body includes a first set of cells; and
   the second media in the channel of the second body includes a second set of cells; wherein the method further comprises the additional step of observing the interaction of the first and second sets of cells after the step of bringing the drop at the output of the channel of the first body into contact with the drop at the input of the channel of the second body.

* * * * *